United States Patent [19]

Maher et al.

[11] Patent Number: 5,393,207
[45] Date of Patent: Feb. 28, 1995

[54] BLOOD PUMP WITH DISPOSABLE ROTOR ASSEMBLY

[75] Inventors: Timothy R. Maher, Orangevale; Pieter W. C. J. le Blanc, Pollock Pines; Lynn P. Taylor, Camino, all of Calif.

[73] Assignee: Nimbus, Inc., Rancho Cordova, Calif.

[21] Appl. No.: 6,735

[22] Filed: Jan. 21, 1993

[51] Int. Cl.$^6$ ............................................. F04B 17/00
[52] U.S. Cl. .......................... 417/423.7; 417/423.14; 417/53; 415/206; 415/900
[58] Field of Search ........... 417/423.70, 423.8, 423.15, 417/423.11, 423.12, 423.14, 420, 53; 415/900, 206; 604/151; 416/423 B

[56] References Cited

U.S. PATENT DOCUMENTS

| 4,213,742 | 7/1980 | Henshaw | 415/206 |
| 4,826,401 | 5/1989 | Clark et al. | 415/206 |
| 4,898,518 | 2/1990 | Habbard et al. | 417/423.11 |
| 5,017,103 | 5/1991 | Dahl | 417/423.7 |
| 5,145,335 | 9/1992 | Abelen et al. | 417/423.14 |

FOREIGN PATENT DOCUMENTS 0241494  10/1986  Japan ................ 417/423.7

Primary Examiner—Richard A. Bertsch
Assistant Examiner—William J. Wicker
Attorney, Agent, or Firm—Harry G. Weissenberger

[57] ABSTRACT

A centrifugal blood pump features a pump assembly including a cylindrical barrel insertable into a motor stator. The barrel contains a motor rotor which is directly coupled to the pump's impeller. The barrel can be oriented and locked in the motor stator in many different angular orientations. Hemolysis is prevented in spite of high speed operation by reducing the clearance between the impeller and the impeller chamber, rounding the edges of the impeller blades, and providing a deflector to prevent blood from being impelled more than once around the impeller chamber periphery. An efficient releasable locking mechanism is also disclosed, as is a preferred method of assembling the pump assembly with close tolerances.

9 Claims, 8 Drawing Sheets

BLOOD PUMP WITH DISPOSABLE ROTOR ASSEMBLY

FIELD OF THE INVENTION

This invention relates to blood pumps, and more specifically to a centrifugal pump in which the disposable pump element also forms the rotor of the pump motor.

BACKGROUND OF THE INVENTION

Blood pumps used in surgical procedures or other medical applications must of necessity be single-use devices. The cost of the pump motor, however, is prohibitive for a single use. Consequently, blood pumps of this type have conventionally been designed to include a reusable motor and a single-use, disposable pump assembly which could be easily attached to the motor.

The conventional construction of such devices, as illustrated, for example, by U.S. Pat. No. 4,135,253 to Reich et al., transferred power from the motor to the pump rotor through a magnetic clutch. The clutch consisted of a pair of spaced parallel plates, one in the motor housing and one in the pump assembly housing. This construction had several disadvantages: firstly, it was subject to decoupling under sudden load changes; secondly, in order to produce sufficient torque, the bars or plates had to be relatively large, thereby imposing undesirable design constraints on the device; and thirdly, the magnetic clutch made it difficult to obtain an accurate measurement of the actual load on the pump impeller for medical monitoring purposes.

U.S. Pat. No. 4,895,557 to Moise et al. proposed a cable drive for intravascular axial blood pumps in which the driven end of the cable assembly included a disposable motor rotor which, when inserted into the motor stator, provided the drive force for the cable and also the supply conduit for the purge fluid used by the axial pump.

The design constraints referred to above were significant because it is medically necessary to minimize the priming volume of the pump. This in turn requires the pump to be as small as possible. On the other hand, the smaller the pump, the faster it must run to pump an adequate volume of blood. However, the higher the pump speed, the greater the risk of creating significant hemolysis.

SUMMARY OF THE INVENTION

The disposable blood pump of this invention allows the priming volume to be substantially reduced in comparison to conventional pumps, yet produces little or no hemolysis. These objectives are achieved by (1) incorporating the motor rotor directly into the disposable assembly, and (2) providing an impeller and impeller housing configuration which allows substantially higher impeller speeds without creating hemolysis.

For purposes of the first objective, a substantial reduction in the size of the pump is achieved by mounting the motor rotor directly on the shaft of the pump impeller of a disposable centrifugal blood pump assembly. The disposable pump assembly containing the motor rotor is axially insertable into the reusable motor stator so as to provide a direct drive for the pump impeller. This configuration obviates, at least in part, all three of the above-mentioned disadvantages of the prior art. Specifically, the direct drive of the pump impeller dispenses with the magnetic clutch and thereby prevents decoupling. Secondly, the lack of large clutch bars or plates allows the size of the disposable pump assembly to be substantially reduced. This is important not only for cost reasons, but also for safety reasons because a smaller pump de-primes at a lower air bolus, and because the smaller dwell time of the blood on the impeller blades helps in reducing hemolysis. Thirdly, the current drawn by the constant-speed synchronous motor used in these devices is an accurate measure of impeller load due to the directness of the drive.

In another aspect of the invention, hemolysis is further reduced and essentially eliminated by configuring the impeller to have extremely small clearances in the impeller chamber, and to be rounded along its inlet and outlet edges. The impeller housing is so configured as to provide a single path through the pump, so that no part of the blood can make more than a single circumferential pass around the impeller chamber.

The small clearance between the impeller and the impeller chamber is made possible by a novel fabrication method which involves first aligning the impeller with the impeller housing, and then adhesively securing the impeller shaft to a bearing-forming sleeve to maintain the alignment.

DESCRIPTION OF THE PREFERRED EMBODIMENT

Figure 1:
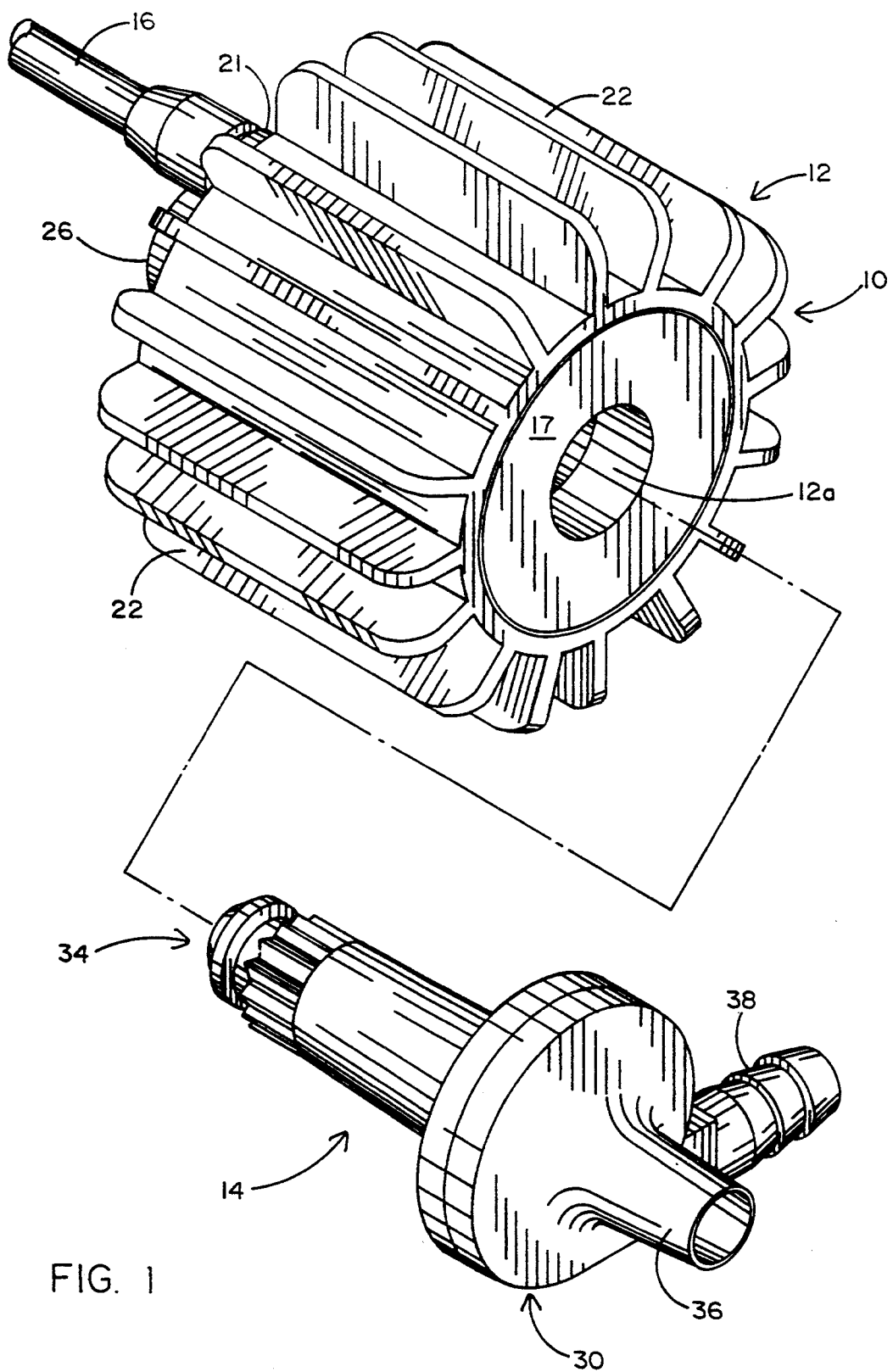
FIG. 1 is a perspective view of the blood pump of this invention showing the reusable and disposable portions of the pump separated.
Figure 2:
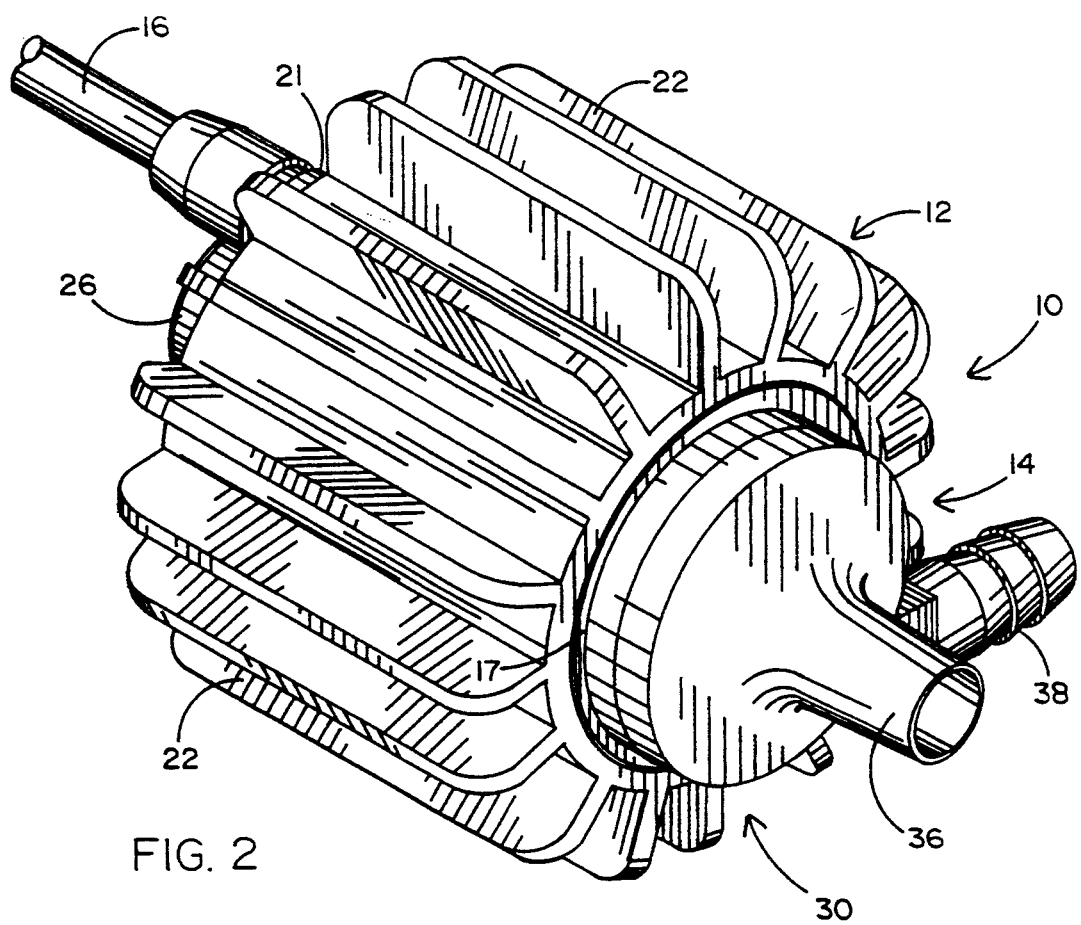
FIG. 2 is a view similar to FIG. 1 but showing the reusable and disposable portions assembled together.
Figure 3:
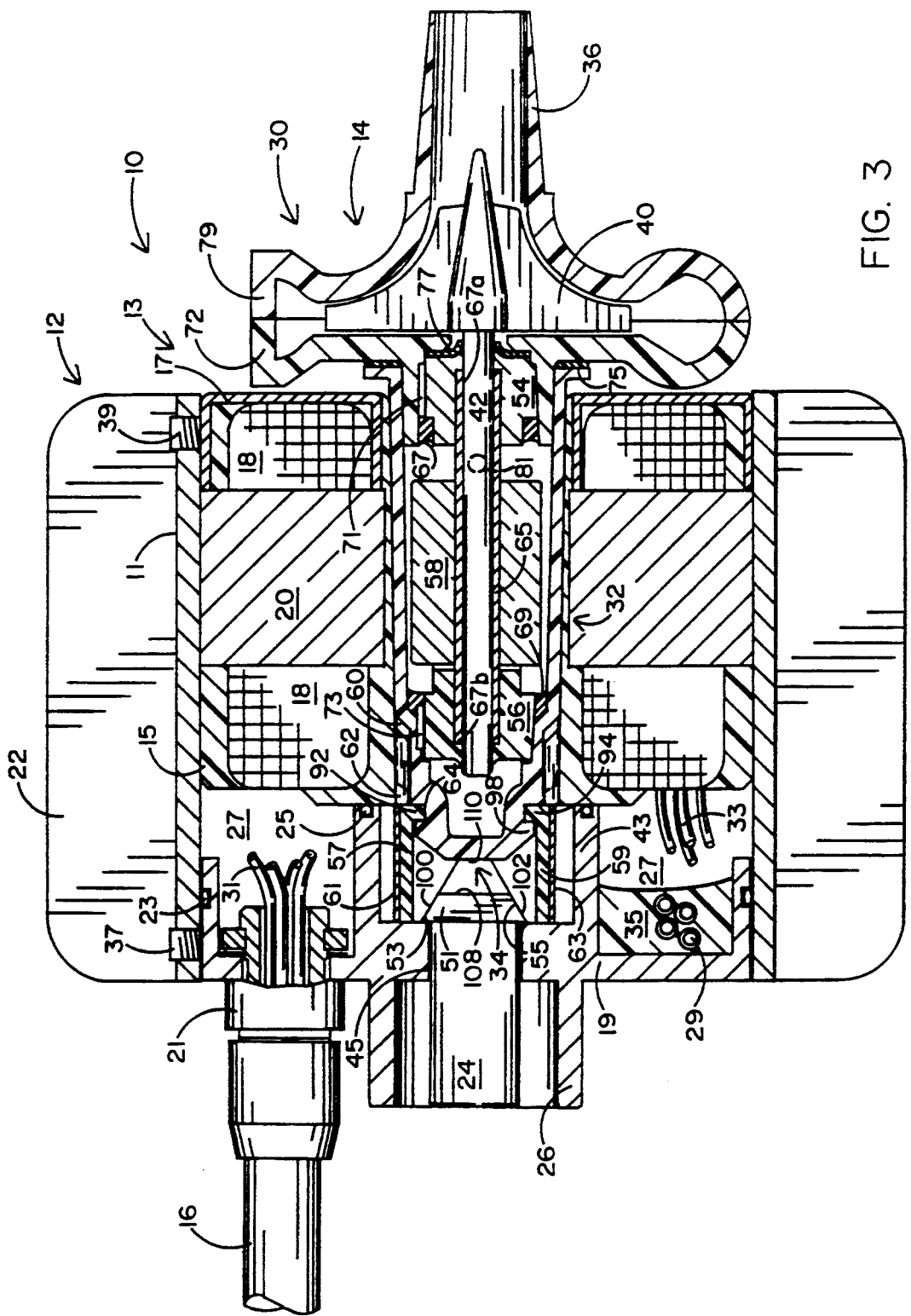
FIG. 3 is an axial cross section of the assembled pump.

FIG. 1 shows the pump 10 of this invention. The pump 10 consists of a reusable motor stator assembly 12 which defines a generally cylindrical cavity 12a, and a disposable pump assembly 14 which can be inserted into that cavity as shown in FIG. 2. The motor stator assembly 12 may be suitably mounted in proximity to an oxygenator (not shown), and powered from an appropriate control console (not shown) through an electric cable 16. The assembly 12 includes a cylindrical metallic housing 11 equipped with cooling fins 22. As shown in FIG. 3, a conventional motor stator 13 including stator windings 18 and stator iron 20 encased in potting 15 is disposed at one end of the housing 11. Embedded in the potting 15 is an electromagnetic interference (EMI)

shield 17, which surrounds the windings 18 at the housing end.

The other end of the housing 11 is closed off by a metallic base plate 19 equipped with a cable fitting 21 through which the cable 16 enters the stator assembly 12. When the base plate 19 is fully inserted into the housing 11 against the potting 15, O-ring seals 23, 25 seal the wiring chamber 27 off from the exterior of stator assembly 12 and from the pump assembly 14. This prevents moisture from penetrating into the wiring chamber 27. As an additional precaution, the solder connections 29 between the cable wires 31 and the motor leads 33 are encased in a separate potting 35 anchored in the wiring chamber 27.

The setscrews 37, 39 lock the motor stator 13 and the base plate 19 in the housing 11 and establish a firm electrical contact between the housing 11, base plate 19, and EMI shield 17. As a result, all metallic parts of the stator assembly 12 are tied together to provide EMI shielding and grounding (through an appropriate ground wire connection, not shown, to cable fitting 21) all around the stator assembly 12.

Figure 8:
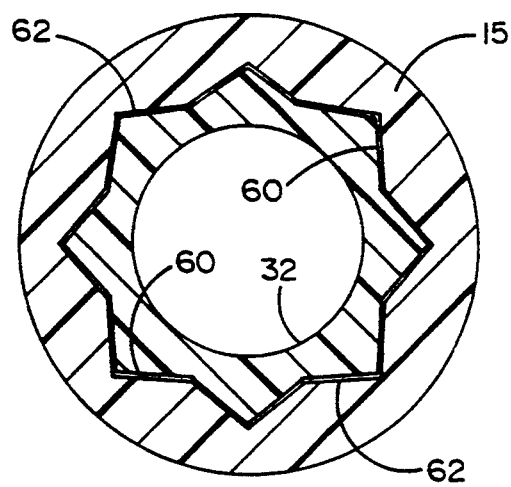
FIG. 8 is a detail cross section along line 8—8 of FIG. 5.

The potting 15 has a set of recesses 62 (best shown in FIG. 8) formed therein for a purpose described below. The base plate 19 includes a square boss 43 in whose center an opening 45 receives a release button 24. The outer end of release button 24 is surrounded by a protective shield 26 to prevent its accidental actuation.

The release button 24 has an elongated wedge-shaped head 51. The head 51 engages corresponding wedge surfaces 53, 55 of slides 57, 59 which are biased toward each other by leaf springs 61, 63 for a reason discussed below.

The disposable pump assembly 14 includes an impeller housing 30 and a pump barrel 32 ending in a locking cap 34. The impeller housing 30 has a blood inlet 36 at the top, and a blood outlet 38 (FIG. 9) at its periphery. It contains an impeller 40 (preferably of the configuration shown in FIGS. 3, 9 and 11) mounted for rotation by the impeller shaft 42. A sleeve 65 is disposed around the impeller shaft 42. The ends 67a, 67b of sleeve 65, together with the bearing blocks 54, 56 constitute the thrust bearings for the impeller 40. The sleeve 65 carries on its outer surface the rotor 58 which is simply a strong cylindrical magnet.

The bearing blocks 54, 56 are secured to the impeller housing 30 and barrel 32, respectively, by adhesive beads 67, 69 and are locked against rotation by anti-rotation ribs 71, 73. The barrel 32, in turn, is bonded to the impeller housing 30 by adhesive bead 75. In order to accurately obtain the desired minimal clearance (0.25–0.5 mm) between the base of impeller 40 and the impeller housing 30, as well as the optimum bearing clearances, the impeller shaft 42, with the impeller 40 attached, is first inserted into the inner portion 72 of the impeller housing 30 and through the resilient seal washer 77 and bearing block 54. A temporary shim (not shown) is placed under the impeller 40 to limit its movement toward portion 72 to the proper clearance. The sleeve 65 is next slipped over the shaft 42 and is cemented to shaft 42 by introducing an appropriate bonding agent through the opening 81 in sleeve 65. Next, the assembly thus produced is pushed into the barrel 32, with the sleeve 65 going into the bearing block 56, as far as it will go. The assembly is then slightly withdrawn to provide proper clearance for thrust bearings 67a and 67b, and the impeller housing portion 72 is cemented to the barrel 32 with the adhesive bead 75. Finally, the temporary shim is removed, and the outer portion 79 of the impeller housing 30 is cemented to the inner portion 72.

As previously mentioned, the sleeve 65 supports the cylindrical motor rotor 58. Together, the stator windings 18, stator iron 20, and rotor 58 form a constant-speed synchronous motor which directly drives the impeller shaft 42 when the pump assembly 14 is inserted into the stator assembly 12. Because the current drawn by a synchronous motor is a function of its load, and because the pump 14 is directly coupled to the motor rotor 58, the pressure head against which the pump 14 is working can be accurately measured at all times by monitoring the current drawn by the stator windings 14. This provides physiologically important data to the medical user.

The impeller housing 30, barrel 32, and bearing blocks 54, 56 are preferably adhesively secured together upon assembly to form an integral pump stator which can be easily handled and sterilized. When the pump assembly 14 is inserted into the motor stator assembly 12, the pump assembly 14 is held against rotation by star-shaped locking teeth 60 formed on the barrel 32, which engage corresponding recesses 62 in the motor stator assembly 12. The provision of the star-shaped teeth 60 makes it possible to orient the pump 14 in eight different positions for optimum orientation. It should be understood that in actual use, the blood pump 10 lies on its side, with the blood outlet 38 pointing down, so that air boluses will collect in the top of the impeller housing 30.

The locking mechanism (FIGS. 4–7) for releasably retaining pump assembly 14 in the motor stator assembly 12 includes a pair of slides 57, 59 biased toward each other by leaf springs 61, 63. The slides 57, 59 are disposed in a square boss 43 formed in the base plate 19 in such a manner that they can slide freely in a direction transverse to the axis of the stator assembly 12 but cannot move axially once the base plate 19 is positioned against the potting 15.

The slides 57, 59 are equipped with flanges 92, 94 which are adapted to engage a groove 64 formed on the barrel 32. When the pump assembly 14 is inserted into the motor stator assembly 12, the inclined face 96 of barrel 32 engages the flanges 92, 94 and pushes the slides 57, 59 radially outwardly against the bias of leaf springs 61, 63, so that the flanges 92, 94 will clear the surface 98 of barrel 32. When the pump assembly 14 is fully inserted, the flanges 92, 94 snap into the groove 64 and lock the pump assembly 14 in the motor stator assembly 12.

When it is desired to release the pump assembly 14, release button 24 is pushed toward barrel 32. A shield 26 is provided on base place 19 to prevent accidental actuation of release button 24. The inclined surfaces 100, 102 on the head of release button 24 engage wedge surfaces 53, 55 on slides 57, 59 and push them apart until the flanges 92, 94 clear the groove 64. At that point, the surface 108 of the release button 24 contacts the surface 110 of barrel 32 and pushes the barrel 32 outwardly enough to prevent reengagement of the flanges 92, 94 with the groove 64.

Figure 9:
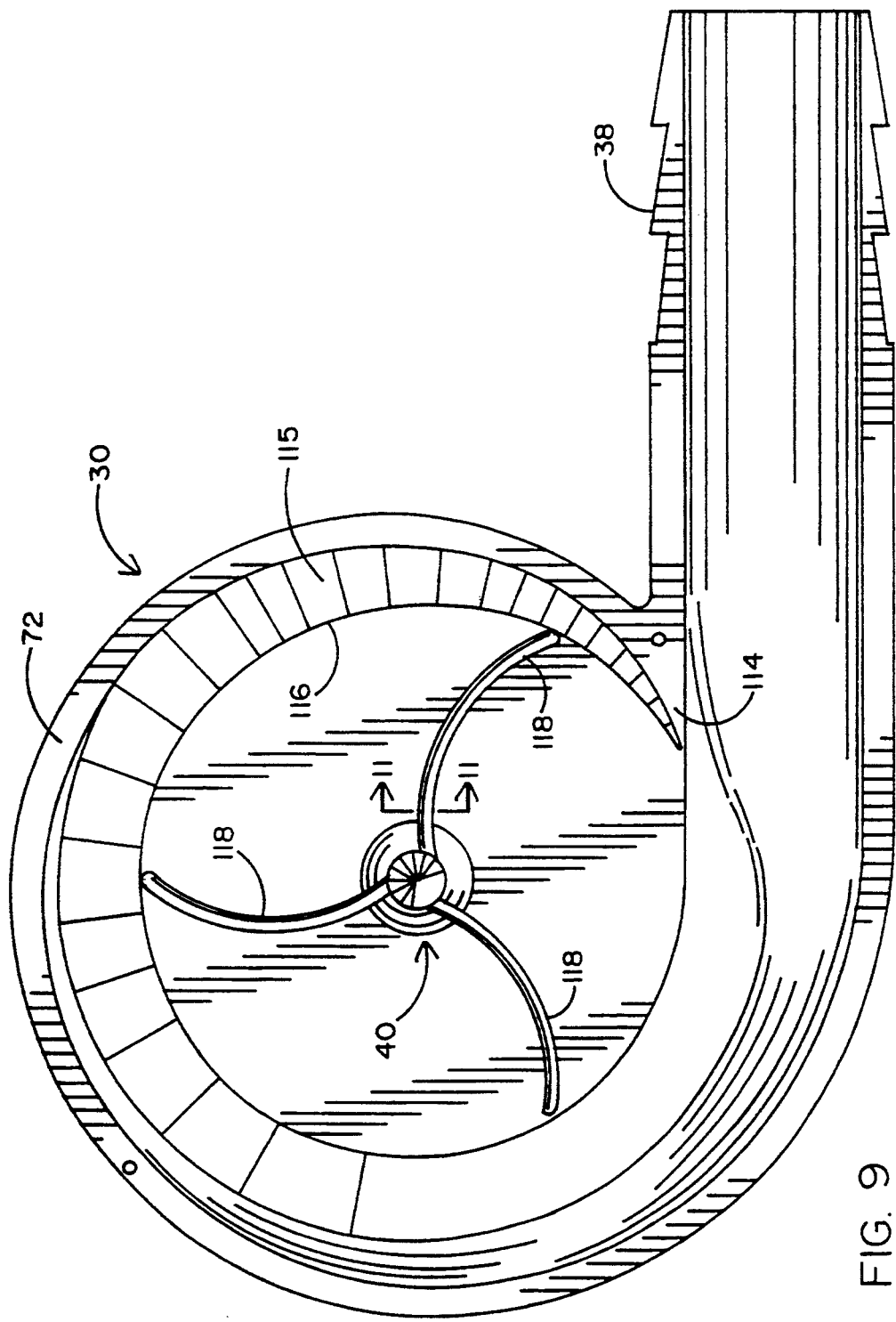
FIG. 9 is a plan view of the impeller and impeller chamber with the outer portion of the impeller chamber removed.
Figure 10:
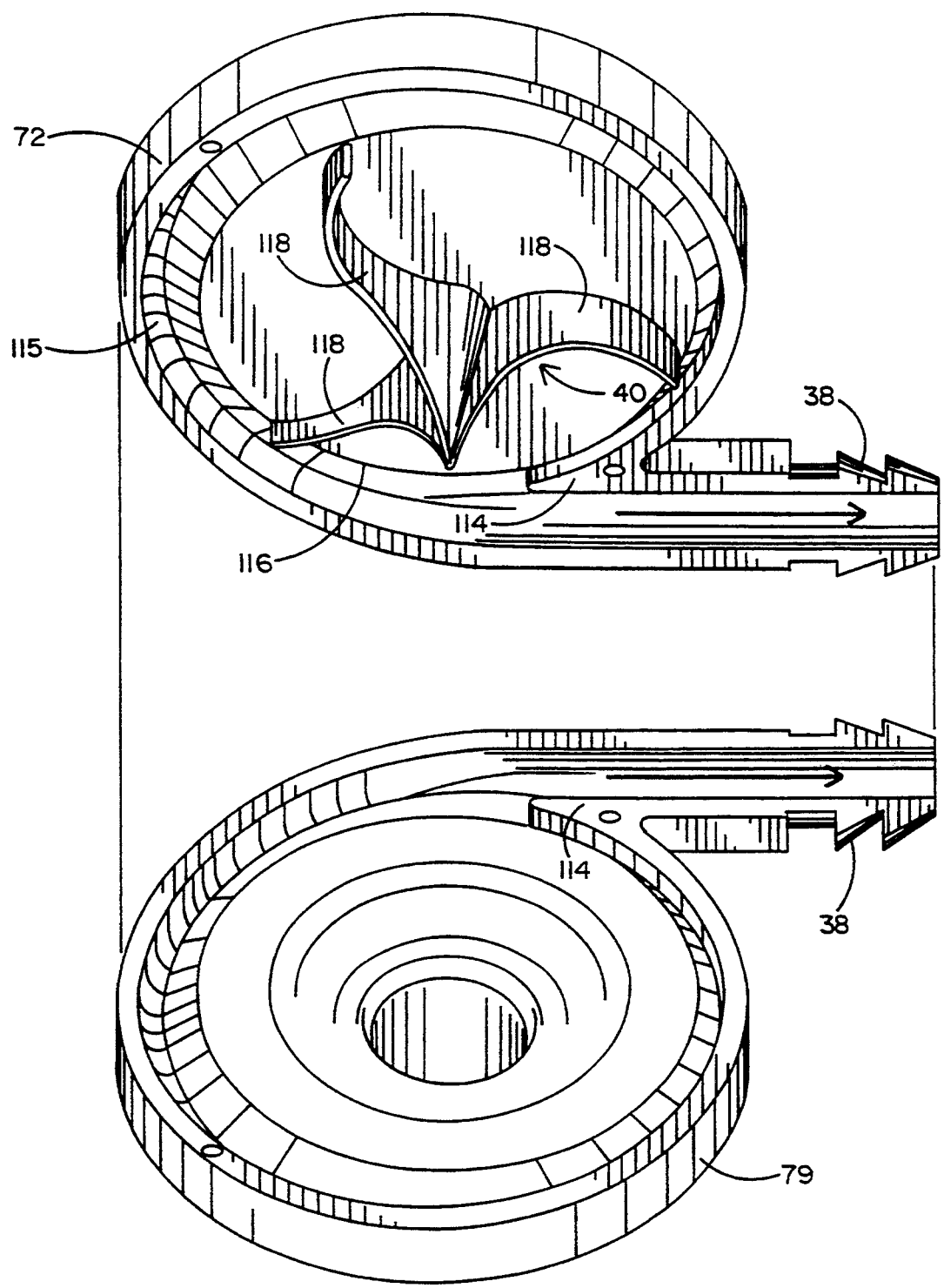
FIG. 10 is an exploded view of the impeller chamber.

A significant feature of the present invention is the configuration of the impeller housing 30 and impeller 40. As best shown in FIGS. 3, 9 and 10, the impeller housing 30 is so shaped as to provide a constant pressure blood flow around the impeller housing 30 with a minimum of direction change, and to prevent any blood from being impelled more than once around the periphery of the impeller chamber 30.

Blood enters the impeller chamber 30 through the centrally located axial intake 36 and is distributed essentially evenly around the periphery of impeller chamber 30. In accordance with the invention, the chamber 30 has an inner shape in the form of a progressively radially truncated toroid. Specifically, proceeding counterclockwise from the deflector 114 in FIG. 9, the volume of the blood channel 115 lying outwardly of the locus of rotation 116 of the outer ends of impeller blades 118 begins with essentially zero, and increases circumferentially of the impeller chamber 30 until it reaches essentially the size of the blood outlet 38 as it approaches the deflector 114. The purpose of deflector 114 is to direct all the blood in the blood channel 115 into the blood outlet 38, and to prevent any recirculation of the blood through the blood channel 15. This is important in minimizing hemolysis.

The linear area change achieved by the illustrated configuration of the blood channel 15 makes it possible to maintain a smooth pressure distribution within the chamber 30, which is another factor in reducing hemolysis.

Figure 4B:
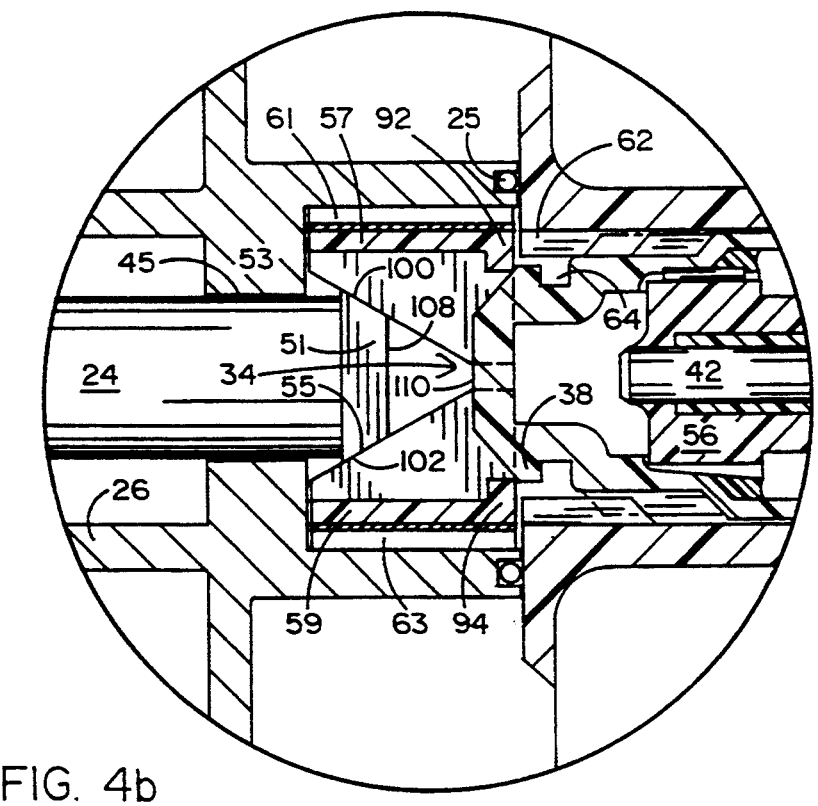
FIG. 4a and 4b are detail views illustrating the insertion of the pump barrel into the locking mechanism.
Figure 4A:
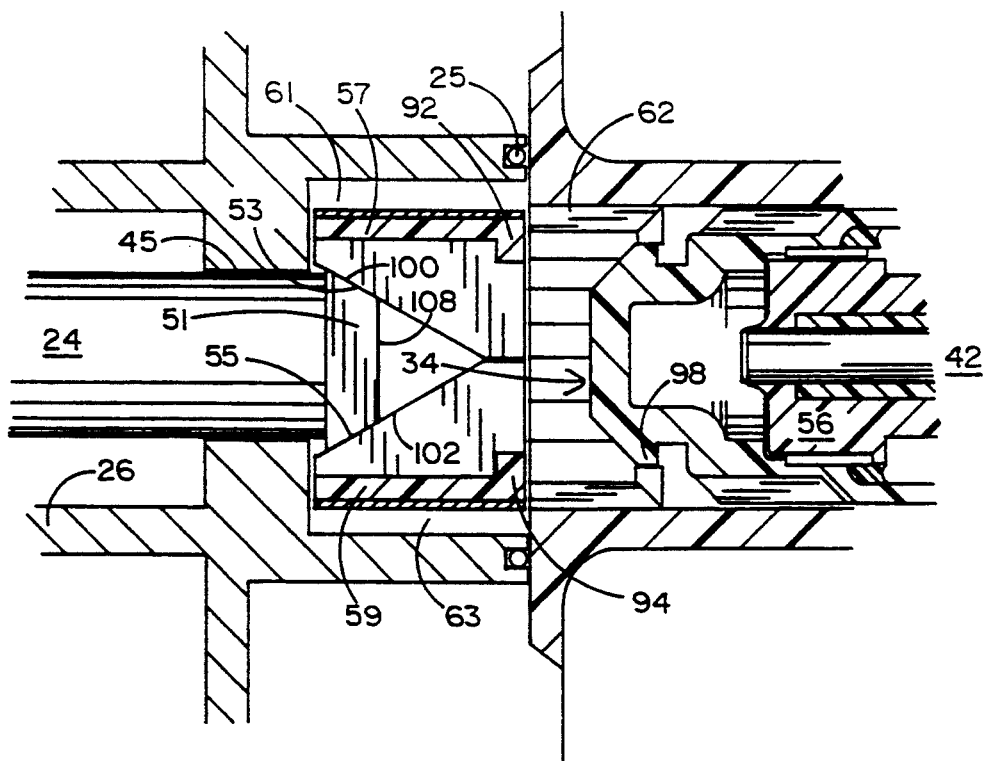
Figure 5:
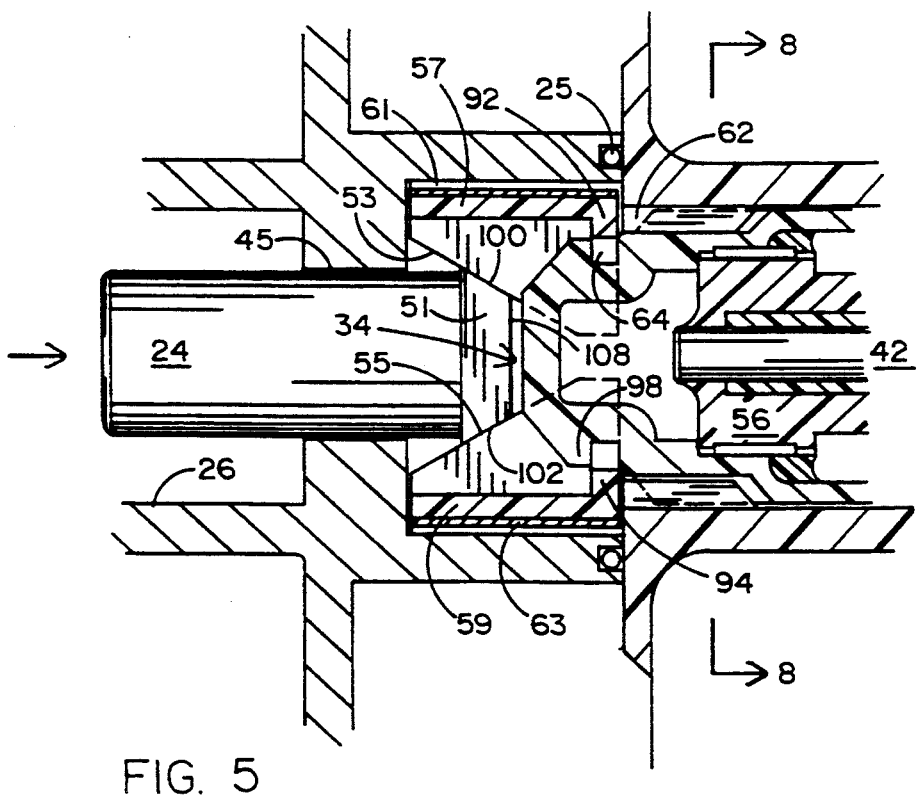
FIG. 5 is a detail view illustrating the release of the locking mechanism.
Figure 6:
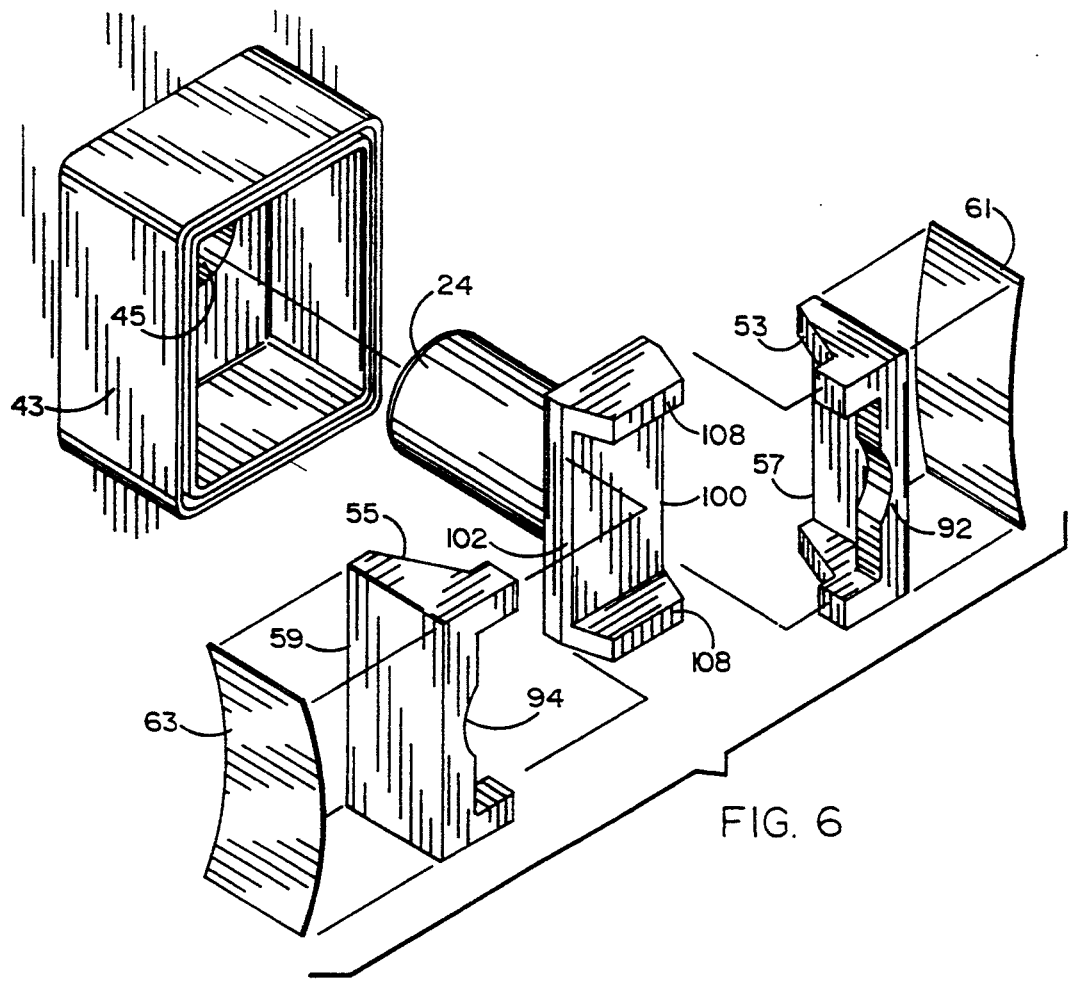
FIG. 6 is an exploded view showing the parts of the locking mechanism.
Figure 7:
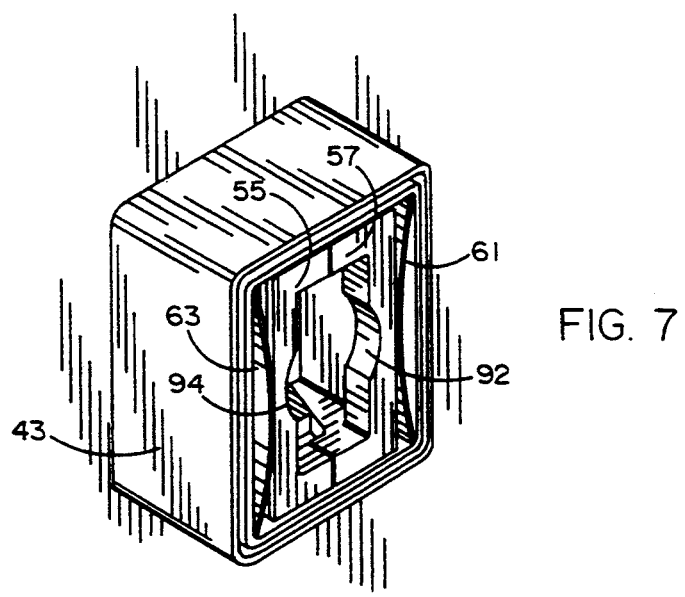
FIG. 7 is a perspective view of the packed locking mechanism.

FIGS. 3-5 illustrate the preferred embodiment of the impeller 40. Although the impeller blades 116 may have radially straight tips, it is preferable to keep them curved. This increases the impeller's blood-propelling efficiency (producing more pressure at lower speeds), which is important in order to obtain adequate flow rates without excessively high impeller speeds, in spite of the small size of the pump. Typical flow characteristics for a representative pump of the type described herein would be about 7.0 l/min against a 500 mm head at 7,500 rpm (as opposed to about 3,600 rpm in conventional centrifugal blood pumps).

Figure 11:
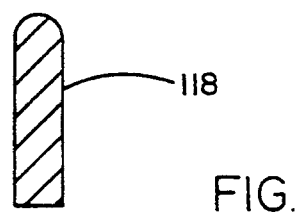
FIG. 11 is a cross section of an impeller blade along line 11—11 of FIG. 9.

Efficiency is further improved in the pump of this invention by maintaining a very small clearance between the impeller blades 116 and the inner portion 75 of the impeller chamber 30. Typically, that clearance in the inventive device is on the order of 0.25–0.5 mm, as opposed to twice that amount in conventional centrifugal blood pumps. The smaller clearance is made possible without causing hemolysis by rounding the inlet and outlet edges of the impeller blades, i.e. by making the cross section of the blades 116 at their edges half-circles as illustrated in FIG. 11.

The above-described construction allows the manufacture of a blood pump with a priming volume of only about 10–15 cc (as opposed to about 40 cc in conventional centrifugal blood pumps) without sacrificing throughput and without producing significant hemolysis—a considerable improvement in this delicate art.

We claim:

1. A blood pump, comprising:
   a) a reusable motor stator assembly including a motor stator defining a substantially cylindrical cavity;
   b) a disposable pump assembly including:
      i) a substantially cylindrical barrel adapted to be inserted in and withdrawn from said cavity;
      ii) motor rotor means disposed in said barrel for rotation with respect thereto, said motor rotor means being so positioned in said barrel as to cooperate with said motor stator to form an electric motor when said barrel is inserted into said cavity;
      iii) a centrifugal blood pump including an impeller, said impeller being directly connected to said motor rotor for rotation therewith; and
      iv) releasable locking means operable to releasably lock said barrel in engagement with said cavity without rotation of said barrel.

2. The blood pump of claim 1, further comprising:
   c) cooperating orientation means on said pump assembly and said stator assembly, said orientation means being arranged to allow insertion of said pump assembly into said stator assembly in any of a plurality of orientations, and to hold said pump assembly against rotation with respect to said stator assembly when so inserted.

3. The blood pump of claim 1, in which said releasable locking means are positioned on said stator assembly and are arranged to engage said pump assembly when fully inserted and to prevent longitudinal movement of said pump assembly when so engaged.

4. The blood pump of claim 1, in which said impeller has an impeller shaft, said shaft being surrounded by a sleeve fixedly attached to said shaft, said sleeve carrying said motor rotor, and in which said pump assembly includes therein a pair of bearing blocks, the ends of said sleeve forming thrust bearings with said bearing blocks.

5. The blood pump of claim 1, in which said impeller is rotatable within an impeller housing, and the clearance between said impeller and said impeller housing is substantially 0.25–0.5 mm.

6. The blood pump of claim 5, in which said impeller has impeller blades, and the inlet and outlet edges of said blades are rounded.

7. A blood pump comprising:
   a) a reusable motor stator assembly: including a motor stator defining a substantially cylindrical cavity;.
   b) a disposable pump assembly including:
      i) a substantially cylindrical barrel adapted to be inserted in and withdrawn from said cavity;
      ii) motor rotor means disposed in said barrel for rotation with respect thereto, said motor rotor means being so positioned in said barrel as to cooperate with said motor stator to form an electric motor when Said barrel is inserted into said cavity;
      iii) a centrifugal blood pump including an impeller, said impeller being directly connected to said motor rotor for rotation therewith; and releasable locking means operable to releasably lock said barrel in engagement with said cavity without rotation of said barrel;
      iv) said releasable locking means being positioned on said stator assembly and being arranged to engage said pump assembly when fully inserted and to prevent longitudinal movement of said pump assembly when so engaged;
      v) said releasable locking means including:
         1) a substantially circumferential groove formed on said pump assembly;
         2) a pair of locking members movable in a direction transverse to the direction of insertion of said pump assembly and having flange means engageable with said groove for locking said pump assembly against longitudinal movement;
         3) said locking members being resiliently biased into locking engagement with said groove, and having a wedge surface formed thereon; and 4) a release button having a head positioned between said locking members, said head having formed thereon a pair of wedge surfaces engageable with said wedge surfaces of said locking members to move said locking members out of engagement with said groove when said release button is depressed;

5) said head further having a surface engageable with said pump assembly to longitudinally move said pump assembly sufficiently upon depression of said release button to prevent reegagement of said locking means with said groove when said release button is released.

8. A blood pump, comprising:
a) a reusable motor stator assembly including a motor stator defining a substantially cylindrical cavity; and
b) a disposable pump assembly including:
   i) a substantially cylindrical barrel adapted to be releasably inserted in said cavity;
   ii) motor rotor means disposed in said barrel for rotation with respect thereto, said motor rotor means being so positioned in said barrel as to cooperate with said motor stator to form an electric motor when said barrel is inserted into said cavity; and
   iii) a centrifugal blood pump including an impeller housing fixed to said barrel and enclosing an impeller, said impeller being directly connected to said motor rotor for rotation therewith.

9. A method of assembling a close-tolerance disposable blood pump, comprising the steps of:
a) forming a generally cylindrical barrel;
b) fixing in said barrel a first bearing block having a substantially cylindrical opening therethrough and a substantially annular first shoulder formed within said opening;
c) providing an impeller chamber having an inner and an outer portion, and having a second bearing block fixed thereto, said inner portion and second bearing block having substantially cylindrical co-axial openings formed therethrough, a substantially annular second shoulder being formed in said opening in said second bearing block;
d) providing an impeller mounted on an impeller shaft;
e) inserting said impeller shaft through said openings in said impeller chamber inner portion and said second bearing block to a depth where said impeller is spaced from said impeller chamber inner portion by a desired distance;
f) slipping onto said impeller shaft a sleeve carrying a motor rotor, said sleeve being so dimensioned as to be insertable into said opening of said second bearing block but only as far as said second shoulder;
g) positioning said sleeve in said second bearing block so that its one end is spaced from said second shoulder by a predetermined bearing clearance;
h) fixing said sleeve to said impeller shaft;
i) inserting said impeller shaft and sleeve into said first bearing block to a position wherein the other end of said sleeve is spaced from said first shoulder by a predetermined bearing clearance;
j) fixing said inner portion of said impeller chamber to said barrel in the position so defined; and
k) fixing said outer portion of said impeller chamber to said inner portion thereof.

* * * * *